United States Patent [19]

Blythin et al.

[11] Patent Number: 4,684,727

[45] Date of Patent: Aug. 4, 1987

[54] ZWITTERIONIC 1,8-NAPHTHYRIDINE AND PYRAZINO[2,3-B]PYRIDINE CONTAINING COMPOUNDS USEFUL AS ANTI-ALLERGIC, ANTI-INFLAMMATORY AND CYCLOPROTECTIVE AGENTS

[75] Inventors: David J. Blythin, North Caldwell; Ho-Jane Shue, Pine Brook, both of N.J.

[73] Assignee: Schering Corporation, Kenilworth, N.J.

[21] Appl. No.: 760,196

[22] Filed: Jul. 29, 1985

[51] Int. Cl.$^4$ .................... A61K 31/44; C07D 471/04
[52] U.S. Cl. .................................. 544/127; 544/117; 544/212; 544/238; 544/295; 544/333; 544/350; 544/362; 540/520; 546/122/ 546/134; 546/136; 546/137; 546/155
[58] Field of Search ............. 546/122, 155, 136, 134, 546/137, 126; 544/350, 212, 238, 333, 117, 127, 362, 295; 540/520; 514/249, 300, 304, 305, 312, 216, 232, 239, 242, 253, 256

[56] References Cited

PUBLICATIONS

Kappe et al., Monatshefte für Chemie, 99, pp. 2157–2166 (1968).
Merchant et al., Curr. Sci., 49(1), pp. 20–21, (1980); Chem. Abst. vol. 92-181059u (1980).
Wittmann et al., Z. Naturforsch., B: Anorg. Chem., Org. Chem., 33B(12), pp. 1540–1546 (1978); Chem. Abst. vol. 90-121339 (1979).
Bowman et al., "The Synthesis of Some Dialkylamino-2-quinolones," *Journal of the Chemical Society,* pp. 1350–1353 (1964).

Primary Examiner—Henry R. Jiles
Assistant Examiner—Bernard I. Dentz
Attorney, Agent, or Firm—James R. Nelson; Stephen I. Miller; Richard C. Billups

[57] ABSTRACT

Zwitterionic bicyclic compounds are disclosed which are useful as anti-allergic, anti-inflammatory and/or cytoprotective agents. Pharmaceutical compositions and methods of treatment employing such compounds are also disclosed.

11 Claims, No Drawings

ZWITTERIONIC 1,8-NAPHTHYRIDINE AND PYRAZINO[2,3-B]PYRIDINE CONTAINING COMPOUNDS USEFUL AS ANTI-ALLERGIC, ANTI-INFLAMMATORY AND CYCLOPROTECTIVE AGENTS

BACKGROUND OF THE INVENTION

The present invention relates to certain zwitterionic bicyclic compounds and to pharmaceutical compositions and methods of use employing such compounds.

An article by Bowman et al. entitled "The Synthesis of Some Dialkylamino-2-quinolones," *Journal of the Chemical Society,* pp. 1350–1353 (1964), discloses certain 1-alkyl-3-dialkylamino-4-hydroxy-2-quinolones. Mentioned in this article are 3-dimethylamino-4-hydroxy-1-phenyl-2-quinolone and 1-benzyl-3-dimethylamino-4-hydroxy-2-quinolone. No utility is mentioned in the article for such compounds.

SUMMARY OF THE INVENTION

The invention sought to be patented in its pharmaceutical composition aspect comprises a compound having the structural formula I

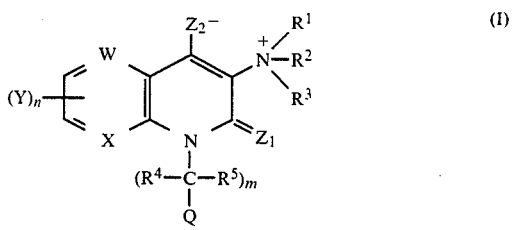

or pharmaceutical acceptable salts thereof, in a combination with a pharmaceutically acceptable carrier, wherein:

W and X may be the same or different and each independently represents —CH= or —N=;

$Z_1$ and $Z_2$ are the same or different and each independently represents —O— or —S—;

$R^1$, $R^2$, $R^3$, $R^4$ and $R^5$ are the same or different and each may be independently selected from the group consisting of H, alkyl having from 1 to 12 carbon atoms, alkenyl having from 3 to 8 carbon atoms, alkynyl having from 3 to 8 carbon atoms, alkoxyalkyl having from 1 to 6 carbon atoms in the alkoxy portion and from 2 to 6 atoms in the alkyl portion thereof, hydroxyalkyl having from 2 to 8 carbon atoms, cycloalkyl having from 3 to 8 carbon atoms, acyloxyalkyl having from 1 to 6 carbon atoms in the acyloxy portion and from 2 to 8 carbon atoms in the alkyl portion thereof, and —$R^6$—$CO_2R^0$ wherein $R^6$ represents an alkylene group having from 1 to 6 carbon atoms and $R^0$ represents hydrogen or an alkyl group having from 1 to 6 carbon atoms, with the provisos that the OH of the hydroxyalkyl group and the acyloxy of the acyloxyalkyl group are not joined to the same carbon atom as another heteroatom and that, when $R^1$, $R^2$ and/or $R^3$ are alkenyl or alkynyl, there is at least one carbon-carbon single bond between the nitrogen atom and the carbon-carbon double or triple bond;

in addition, one of $R^1$, $R^2$ or $R^3$ can be an aryl group or a heterocyclic group, either of which can be substituted with one to three substituents Y as defined below;

in further addition, two of $R^1$, $R^2$ and $R^3$ can be joined together to represent a ring which can contain from 2 to 8 carbon atoms, said ring optionally containing a —O—, —S— and/or —$NR^4$— heteroatomic group (wherein $R^4$ is as defined above) and/or optionally containing a carbon-carbon double bond, and said ring optionally being substituted with one to three additional substituents $R^7$ which substituents may be the same or different and are each independently selected from OH with the proviso that OH is not on a carbon already joined to a hetero atom, —O—acyl having from 1 to 6 carbon atoms, hydroxyalkyl having from 1 to 8 carbon atoms, alkoxyalkyl having from 1 to 6 carbon atoms in each alkyl portion thereof, alkyl having from 1 to 6 carbon atoms, alkenyl having from 3 to 8 carbon atoms, alkynyl having from 3 to 8 carbon atoms, or any two $R^7$ substituent groups may represent a hydrocarbon ring having from 4 to 8 total carbon atoms; and in still further addition, all three of $R^1$, $R^2$ and $R^3$ can be joined together to represent a polycyclic ring, which polycyclic ring can optionally be substituted by one to three substituent groups $R^7$ as defined above;

m is an integer of from 0 to 3;

n is an integer of from 0 to 2;

Q represents an aryl or an aromatic heterocyclic group which can optionally be substituted with 1 to 3 substituents Y as defined below; and each Y substituent is independently selected from the group consisting of hydroxy, alkyl having from 1 to 6 carbon atoms, halogen, $NO_2$, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, hydroxyalkyl having from 1 to 6 carbon atoms, —$S(O)_n$—$R^8$ (wherein $R^8$ represents alkyl having from 1 to 6 carbon atoms and n is as defined above), —$SO_2NH_2$, —CO—$R^9$ (wherein $R^9$ represents OH, —NH—$R^8$ or —O—$R^8$, where $R^8$ is as defined above), —O—B—$COR^9$ (wherein B represents an alkylene group having from 1 to 4 carbon atoms and $R^9$ is as defined above), —$NH_2$, —NH-CHO, —NH—CO—$R^9$ (wherein $R^9$ is as defined above, with the proviso that it is not hydroxy), —NH—$COCF_3$, —NH—$SO_2R^8$ (wherein $R^8$ is as defined above), and —$NHSO_2CF_3$.

A preferred subgenus of compounds is represented by those compounds in which at least one of W and X is N. More preferably, W is CH and X is N. Moreover, at least one of $Z_1$ and $Z_2$ is preferably O and m and n are preferably 0.

An additional preferred subgenus of compounds is represented by the structural formula II

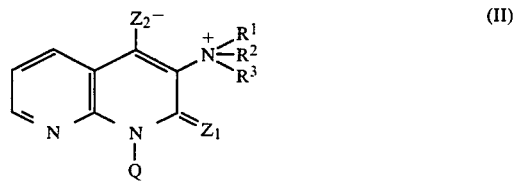

wherein $R^1$, $R^2$, $R^3$, Q, $Z_1$ and $Z_2$ are as defined above. Preferably, at least one of $Z_1$ and $Z_2$ is O. In addition, Q is preferably an aryl group, which may be optionally substituted with one, to three Y groups, more preferably, one or two Y groups.

The compounds of the invention, because of their zwitterionic character, provide good solubility in physiological fluids, such as blood, plasma, saliva, etc., and in general in polar solvents, such as water and ethanol, which can be used in compositions for delivering the compounds to patients. This characteristic is advantageous in that the compounds are expected to be more easily absorbed gastrointestinally and therefore provide good activity when administered orally.

The invention sought to be patented in a first pharmaceutical method aspect is a method for treating allergic reactions in a mammal which comprises administering an anti-allergic effective amount of the above-defined pharmaceutical composition to the mammal.

The invention sought to be patented in a second pharmaceutical method aspect is a method for treating inflammation in a mammal which comprises administering an anti-inflammatory effective amount of the above-defined pharmaceutical composition to the mammal.

The invention sought to be patented in a third pharmaceutical method aspect is a method for treating peptic ulcers in a mammal which comprises administering a cytoprotective effective amount of the above defined pharmaceutical composition to the mammal.

The invention sought to be patented in its chemical compound aspect is a compound having the structural formula I as defined above with the proviso that 3-dimethylamino-4-hydroxy-1-phenyl-2-quinolone and 1-benzyl-3-dimethylamino-4-hydroxy-2-quinolone are excluded. In another aspect the compounds of the invention may have the structural formula I as defined above with the provisos that $-N^+R^1R^2R^3$ does not represent $-N^+H(alkyl)_2$ when $m=0$, $n=0$, W and X are both $-CH=$, $Q=$phenyl, $Z_1=O$ and $Z_2=O$ or when $m=1$, $n=0$, W and X are both $-CH=$, $R^4$ and $R^5$ are both H, $Q=$phenyl, $Z_1=O$ and $Z_2=O$.

DETAILED DESCRIPTION OF THE INVENTION

The compounds employed in the present invention may be prepared from a compound of structural formula III:

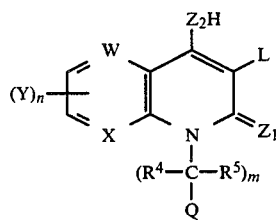

wherein $R^4$, $R^5$, Q, X, Y, W, $Z_1$, $Z_2$, m and n are as defined above and L is a substituent known to those skilled in the art as a "leaving group."

Treatment of compound of the formula III above with the amine compound of the formula

         IV (wherein $R^1$, $R^2$, and $R^3$ are as defined above) with heat in a suitable solvent, such as pyridine, dimethyl formamide, hexamethyl phosphoramide, 2,6-lutidine, dimethyl acetamide or similar solvent. The reaction, depending upon the reactants chosen, can be performed at temperatures of from about 60° C. to the reflux temperature of the particular solvent.

For purposes of the invention, a "leaving group" is defined as a substituent which may be displaced and carry a negative charge. Representative examples of suitable leaving groups include chloride, bromide, iodide, trifluoroacetoxy, methanesulfonyloxy, trifluoromethanesulfonyloxy, p-toluene-sulfonyloxy, $-I^+-Ar$, and the like. A preferred leaving group is bromide.

The compound of formula IV above is generally a secondary or tertiary amine, i.e., one in which at most one of the groups $R^1$, $R^2$ or $R^3$ is hydrogen. Such materials are readily obtainable either commercially or by methods well known to one of ordinary skill in the The intermediates of formula III above are either known or can be prepared from corresponding 3unsubstituted derivatives which are disclosed, for example, in U.S. Pat. No. 4,492,702, the disclosure of which is incorporated herein by reference. For example, a compound of the formula (V)

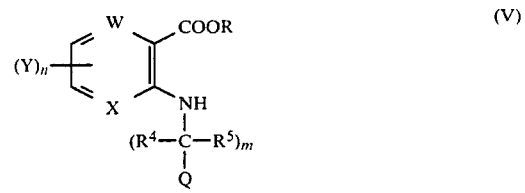

(wherein Q, $R^4$, $R^5$, Y, W, X, n and m are as defined herein and R is any convenient alkyl group) may be reacted with a compound of structural formula VI $$CH_3CO_2R \qquad (VI)$$

(wherein R is again, for example, an alkyl group) to directly produce the compounds of the formula VII

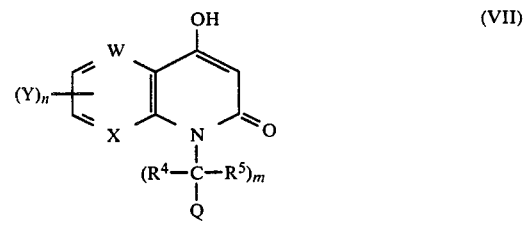

This reaction is preferably accomplished by contacting the two reactants V and VI in the presence of a base such as a metal alkoxide, e.g., potassium tertiary butoxide or the like, at an elevated temperature, e.g., 60° to about 160° C., for a sufficient time until the reaction is substantially completed. The reaction is preferably conducted in an inert atmosphere such as nitrogen. Alternatively, the reaction may be conducted in the presence of a non-reactive solvent such as toluene, xylene, etc.

The compounds of formula VII above can be reacted with a suitable agent to provide the leaving group in the three position on the ring. For example, direct bromination of the compound of formula VII above will provide a compound of III above where L equals Br. As another example, reaction of the compound of VII above with iodosobenzene results in the formation of a compound of formula III where L is $-I^+-Ph$.

The compounds having structural formula I above wherein $Z_1$ and $Z_2$ are oxygen may be converted to the corresponding compounds wherein $Z_1$ and/or $Z_2$ are sulfur by known methods. For example, treatment with Lawesson's Reagent [2,4-bis(4-methoxyphenyl)-1,3-dithia-2,4-diphosphetane-2,4-disulfide] in hot toluene will effect this conversion. The isomeric and tautomeric forms can be provided by chromatography of the reaction mixture.

When utilized herein and in the appended claims the below listed terms are defined as follows:

halogen—fluorine, chlorine, bromine and iodine;
alkyl and alkoxy—comprise straight and branched carbon chains and, unless otherwise specified, contain from 1 to 6 carbon atoms;
alkenyloxy—comprise straight and branched carbon chains and, unless otherwise specified, contain from 3 to 8 carbon atoms and comprising a carbon to carbon double bond;
alkynyloxy—comprise straight and branched carbon chains and, unless otherwise specified, contain from 3 to 8 carbon atoms and comprising a carbon to carbon triple bond;
aryl—a carbocyclic group containing at least one benzene ring, with the aryl groups preferably containing from 6 to 15 carbon atoms, more preferably being phenyl or Y-substituted phenyl, e.g., phenyl, naphthyl, indenyl, indanyl, 4-chlorophenyl, 4-fluorophenyl, etc.;
aromatic heterocyclic—cyclic groups having at least one O, S and/or N heterogroup interrupting the ring structure and having a sufficient number of unsaturated carbon to carbon bonds, nitrogen to carbon bonds, etc., to provide aromatic character, with the aromatic heterocyclic groups preferably containing from 4 to 14 carbon atoms, e.g., pyridyl, furyl, thienyl, thiazolyl, imidazolyl, pyrimidinyl, pyrazinyl, pyridazinyl, 1,2,4-triazinyl, benzofuranyl, indolyl, pyrazolyl, oxazolyl, etc. Many times such heterocyclic groups can be bonded via various positions on the ring and all such variations are contemplated, e.g. 2- or 3-furanyl, 2-, 3- or 4-pyridyl, etc.

The compounds of the invention are comprised of a —$(CR^4R^5)_m$— substituent wherein each $R^4$ group and each $R^5$ group may vary independently. Thus, for example, when m equals 2 the following patterns of substitution (wherein hydrogen and $CH_3$ are used to represent any substituent, $R^4$ or $R^5$,) are contemplated: —$C(CH_3)_2CH_2$—, —$CH_2C(CH_3)_2$—, —$CH_2CH(CH_3)$—, —$CH(CH_3)CH_2$—, —$(C(CH_3)H)_2$— and the like. In addition when m equals 3, substituents such as —$C(CH_3)_2CH(C_2H_5)$—$CH_2$—, —$CH(CH_3)$—$CH_2$—$CH(C_2H_5)$—, and —$CH_2$—$CH(i$—$C_3H_7)CH(C_2H_5)$— are also contemplated.

The $R^1$, $R^2$ and $R^3$ groups on the amino nitrogen in the compounds of the invention can be the same or different. In some instances as noted above, two of such groups or three of such groups may together represent a heterocyclic ring system with the nitrogen of the amino group being part of such ring, e.g., a monocyclic or bicyclic ring. Examples of suitable —$N^+R^1R^2R^3$ groups include a protonated primary amino group —$N^+H_3$; protonated secondary amino groups such as —$N^+H_2(CH_3)$, —$N^+H_2($—$CH_2$—$CH$=$CH_2)$, —$N^+H_2(phenyl)$, —$N^+H_2(4$-pyridyl), etc.; protonated tertiary amino groups such as —$N^+H(CH_3)_2$, —$N^+H(CH_2CO_2H)[C(CH_2OH)_3]$, etc.; quaternary amino groups such as —$N^+(CH_3)_3$, —$N^+(CH_3)_2(phenyl)$ etc.; and protonated quaternary heterocyclic amino groups containing the nitrogen atom in the heterocyclic ring such as pyrrolidinium, 1-methyl pyrrolidinium, piperidinium, 1-methyl piperidinium,

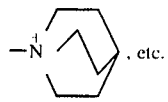, etc.

As noted above, the compounds of the invention may include one to three Y substituents on the bicyclic ring system. Also, the Q group may include one or two Y substituents. In cases where there is more than one such Y substituent, they may be the same or different. Thus, compounds having combinations of different Y substituents are contemplated within the scope of the invention. Examples of suitable Y substituents include OH, methyl, chloro, bromo, methoxy, cyclohexyl, allyloxy, 2-propynyloxy, hydroxyethyl, methylthio, methylsulfonyl, carboxy, acetoxy, N-methylaminocarbonyl, acetoxymethoxy, acetamido, methylsulfonamido and the like.

Exemplary compounds within the scope of the present invention are:

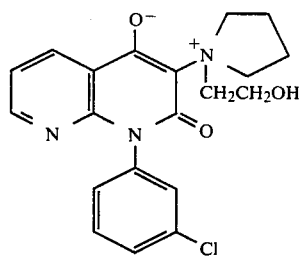

Ia

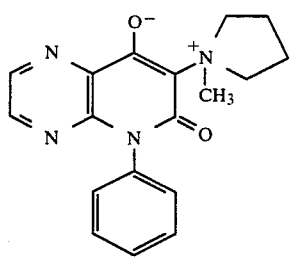

Ib

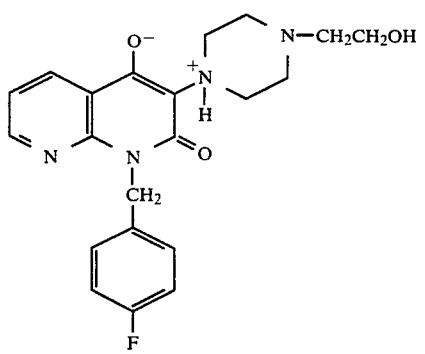

Ic

-continued
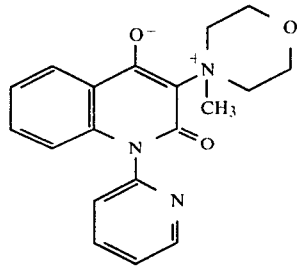 Id
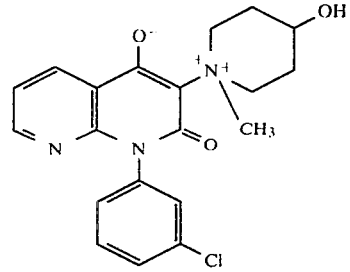 Ij
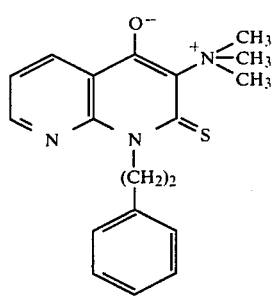 Ie
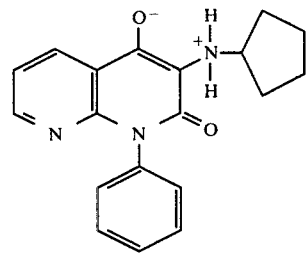 Ik
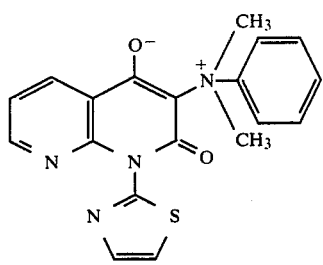 If
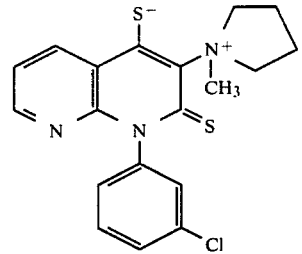 Il
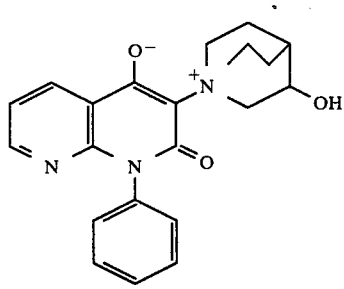 Ig
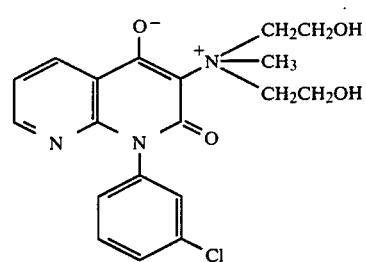 Im
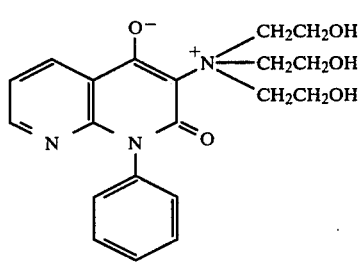 Ih
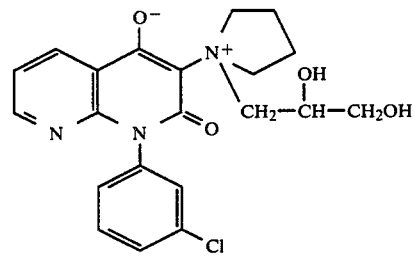 In
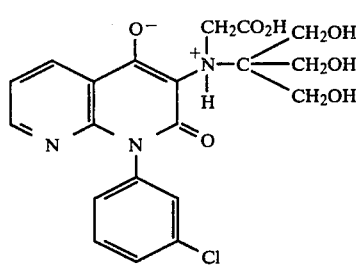 Ii
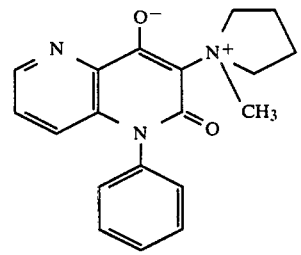 Io

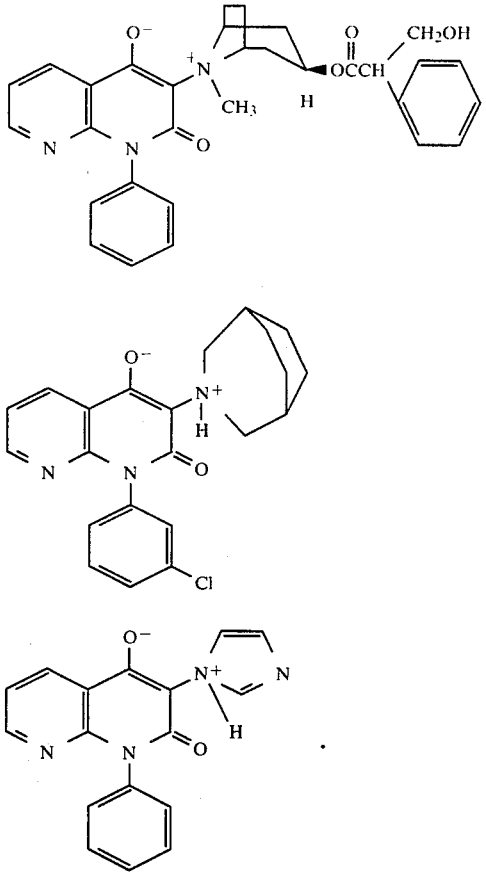

The compounds of the invention are zwitterionic or inner salts, i.e., they are both positively and negatively charged. However, pharmaceutically acceptable salts of such compounds are alos contemplated, i.e., pharmaceutically acceptable acid addition or basic salts. Examples of suitable acid addition salts include the chloride (from hydrochloric acid), methyl sulfate (from methyl sulfuric acid) sulfate (from sulfuric acid) and bromide. Basic salts can be formed when at least one of $R^1$, $R^2$ and $R^3$ is H. Examples of suitable basic salts include sodium, potassium or calcium salts (from their corresponding hydroxides).

The compounds of the invention of formula I can exist in unsolvated as well as solvated forms, including hydrated forms, e.g., a hemihydrate. In general, the solvated forms, with pharmaceutically acceptable solvents such as water, ethanol and the like are equivalent to the unsolvated forms for purposes of the invention.

Certain compounds of. the invention may exist in isomeric and tautomeric forms. The invention contemplates all such isomers and tautomers—the isomers both in pure form and in admixture, including racemic mixtures.

The compounds of the invention may be employed as anti-allergy agents in the treatment of, for example, asthma, allergic or seasonal rhinitis, and/or chronic bronchitis.

The anti-allergy method of this invention is identified by tests which measure a compound's inhibition of anaphylactic bronchospasm in sensitized guinea pigs having antigen induced broncho-constriction.

In one such test procedure, male Hartley guinea pigs (250–300 g) are sensitized with 5 mg ovalbumin injected i.p. and 5 mg injected s.c. in 1 ml saline on day 1 and 5 mg ovalbumin injected i.p. on day 4. The sensitized animals are used 3–4 weeks later at which time they weighed 450–500 g.

The sensitized guinea pigs are fasted overnight and the following morning are anesthetized with 0.9 ml/kg i.p. of dialurethane (0.1 g/ml diallylbarbituric acid, 0.4 g/ml ethylurea and 0.4 g/ml urethane). The trachea are cannulated and the animals are ventilated by a Harvard rodent respirator at 50 strokes/minute with a stroke volume of 5 ml. A side arm to the tracheal cannula is connected to a Harvard pressure transducer to obtain a continuous measure of intratracheal pressure which is recorded on a Harvard polygraph. The jugular vein is cannulated for the i.v. administration of substances. The animals are challenged with antigen (0.5% ovalbumin) as an aerosol generated from a DeVilbiss Model 65 ultrasonic nebulizer and delivered through the tracheal cannual for 30 seconds. Bronchoconstriction is measured as the peak increase in lintratracheal pressure occuring within 5 minutes after antigen challenge.

The sensitized guinea pigs are injected i.v. with 1 mg/kg propranolol, 5 mg/kg indomethacin and 2 mg/kg mepyramine given together in a volume of 1 ml/kg. Fifteen minutes later the animals are challenged with nebulized ovalbumin. Test compounds are administered orally 2 hours before challenge with ovalbumin. Suppression of anaphylactic bronchospasm is expressed as a percent inhibition of the peak increase in intratracheal pressure by comparison to a vehicle-treated control group.

For example, the compound 1-methyl-1-(1,2-dihydro-4-hydroxy-1-phenyl-2-oxo-1,8-naphthyridin-3-yl)-pyrrolidinium-hydroxide, inner salt, hemihydrate, was found to inhibit anaphylactic bronchospasms in such test procedure when given at an oral dose of 1 mg/kg. This compound was also found to inhibit allergen-induced histamine release from guinea pig and human sensitized tissue. The compounds are effective non-adrenergic, non-anticholinergic, antianaphylactic agents. When administered orally they are active at doses from about 0.1 to 10 mg/kg of body weight; when administered parenterally, e.g., intravenously, the compounds are active at dosages of from about 0.05 to 5 mg/kg body weight, when administered by inhalation (aerosol or nebulizer) the compounds are active at dosages of about 0.25 to 5 mg per puff, one to four puffs may be taken every 4 hours.

The compounds of this invention are also useful for the treatment of inflammation. Thus, they are useful in the treatment of arthritis, bursitis, tendonitis, gout and other inflammatory conditions. The anti-inflammatory use of the compounds of the present invention may be demonstrated by the Reversed Passive Arthus Reaction (RPAR) Synovitis technique as set forth below using male Lewis rats (obtained from Charles River Breeding Laboratories) weighing 200–250 grams. The potency of the compounds is determined using indomethacin as the standard. On the basis of the test results, an oral dosage range of about 5 milligrams per kilogram of body weight per day to about 50 milligrams per kilogram of body weight per day in divided doses taken at about 4 hour intervals is recommended.

The dosage to be administered and the route of administration depends upon the particular compound used, the age and general health of the patient and the severity of the inflammatory condition. Thus, the dose ultimately decided upon must be left to the judgment of a trained health-care practitioner.

RPAR Synovitis Technique

A Lewis rat is dosed orally with drug or placebo one hour prior to intravenous administration of 2.28 mg of bovine serum albumin (BSA) in 0.2 cc of pyrogen-free saline followed by the intraarticular injection of 0.54 mg of rabbit anti-BSA antibody in 0.03 cc of pyrogen-free saline into one knee joint. The contralateral knee is injected with 0.03 cc of pyrogen free saline. All injections are made with the animal under light ether anesthesia. Three hours later the rat is again dosed orally with drug or placebo. All drug doses are split. That is, one-half of the dose is administered before lesion induction and one-half is administered after lesion induction.

The following morning (about 17 hours after lesion induction) the rat is killed and both knee joints are exposed. The subpatellar areolar tissue with attendant synovium is excised and weighed. Differences between the weight of antibody and saline injected knees are considered to represent the inflammatory response for each animal (delta synovial weight). Differences in delta synovial weight between lesion controls and drug-treated rats are evaluated for statistical significance with an analysis of variance. Relative potencies are determined with a linear regression analysis.

The compounds of this invention are also useful in the treatment of peptic ulcers. They display chemotherapeutic activity which enables them to relieve the symptoms of peptic ulcer disease, stress ulceration, and promote healing of gastric and/or duodenal ulcers. The antiulcer activity of the compounds of this invention is identified by tests which measure the cytoprotective effect in rats. The compounds are also useful as conjunctive therapeutic agents for coadministration with such antiinflammatory/analgesic agents as aspirin, indomethacin, phenylbutazone, ibuprofen, naproxen, tolmetin and other agents. The compounds of this invention prevent the untoward side effects of irritation and damage to the gastrointestinal tract caused by such agents.

The compounds of this invention are evaluated for their antiulcer activity characteristics by standard biological testing procedures.

In cytoprotective tests in rats in which ethanol is employed to induce gastrointestinal damage, the compounds of this invention are found to be effective at doses of about 0.05–50 mg/kg of body weight per day. Preferably the total dosages are administered in 2–4 divided doses per day.

When administered parenterally, e.g. intravenously, the compounds are administered at a dosage range of about 0.01–10 mg/kg of body weight in single or multiple daily doses.

To treat peptic ulcer disease, and prevent and treat drug-induced gastric ulceration, the active compounds of this invention can be administered in unit dosage forms such as tablets, capsules, pills, powders, granules, sterile parenteral solutions or suspensions, suppositories, mechanical delivery devices, e.g. transdermal, and the like.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of the invention may also be deliverable transdermally. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and to the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following examples are intended to illustrate, but not to limit, the present invention.

EXAMPLE 1

Preparation of
4-hydroxy-1-phenyl-1,8-naphthyridin-2(1H)-one

A mixture of methyl-2-phenylamino nicotinate (75.2 g), n-butylacetate (700 mL) and potassium tert-butoxide (148 g) was stirred and heated gradually to reflux. The mixture was refluxed for 16 hours, after which time it was cooled and pured into water (7 L) with stirring. The resulting mixture was acidified to pH 5 with concentrated HCl when a white solid precipitated. The product was filtered off and air dried. The solid product was then suspended in hexane (3 L), triturated, filtered and washed with fresh hexane. This purification process was repeated using ether (1.5 L). The product was dried to yield 48 g of the desired product, m.p. 312°–314° C.

By a similar procedure, using modifications well known to one skilled in the art, the starting materials
ethyl-2-(pyrazinylamino)-nicotinate,
ethyl-2-(4-pyrimidinylamino)-nicotinate,
ethyl-2-(3-(1,2,4-triazinylamino))-nicotinate, and
ethyl-2-(2-thienylmethylamino)-nicotinate
can to converted to
4-hydroxy-1-(2-pyrazinyl)-1,8-naphthyridin-2(1H)-one,
4-hydroxy-1-(4-pyrimidinyl)-1,8-naphthyridin-2(1H)-one,
4-hydroxy-1-3-(1,2,4-triazinyl))-1,8-naphthyridin-2(1H)-one, and
4-hydroxy-1-(2-thienylmethyl)-1,8-naphthyridin-2(1H)-one, respectively.

EXAMPLE 2

Preparation of 3-bromo-4-hydroxy-1-phenyl-1,8-naphthyridin-2(1H)-one

To a suspension of 4-hydroxy-1-phenyl-1,8-naphthyridin-2(1H)-one (1 g) in $CH_2Cl_2$ (20 mL) was added, dropwise and with stirring, a solution of bromine (0.7 g) in $CH_2Cl_2$ (5 mL). The mixture was stirred at room temperature overnight, after which time the product was filtered off, dried in air and recrystallized from acetonitrile to yield 0.87 g of the product, m.p. >280° C.

By employing a similar procedure to that described in Example 2 above using simple modifications based on practices well-known to one skilled in the art, the compounds
4-hydroxy-(2-pyrazinyl)-1,8-naphthyridin-2(1H)-one,
4-hydroxy-1-(b    4-pyrimidinyl)-1,8-naphthyridin-2(1H)-one,
4-hydroxy-1-(3-(1,2,4-triazinyl))-1,8-naphthyridin-2(1H)-one, and
4-hydroxy-1-(2-thienylmethyl)-1,8-naphthyridin-2(1H)-one
can be converted to
3-bromo-4-hydroxy-1-(2-pyrazinyl)-1,8-naphthyridin-2(1H)-one,
3-bromo-4-hydroxy-1-4-pyrimidinyl)-1,8-naphthyridin-2(1H)-one,
3-bromo-4-hydroxy-1-(3-(1,2,4-triazinyl))-1,8-naphthyridin-2(1H)-one, and
3-bromo-4-hydroxy-1-(2-thienylmethyl)-1,8-naphthyridin-2(1H)-one, respectively.

EXAMPLE 3

Preparation of
1-(1,2-dihydro-4-hydroxy-1-phenyl-2-oxo-1,8-naphthyridin-3-yl)-1-methyl-pyrrolidinium hydroxide, inner salt In dry pyridine (30 mL), 3-bromo-4-hydroxy-1-phenyl-1,8-naphthyridin-2(1H)-one (10 g) was suspended. N-methyl pyrrolidine (20 mL) was added to the suspension. The mixture was heated to 95°–100° C. with stirring, and was kept there for about 33 hours. The product was evaporated under high vacuum to provide a dark oil. This oil was slurried with 200 mL of $CH_3CN(40): H_2O(60): CH_3CO_2H(1)$ and filtered. The solid residue on the filter was rinsed with water and the filtrate was evaporated to remove most of the $CH_3CN$. Reversed phase chromatography through an E. Merck RP-8 LoBar column, eluting with increasing concentrations of $CH_3CN$ in $H_2O$ (containing 1% $CH_3CO_2H$) gave a moderately pure product which was subjected to a second chromatographic separation using the same conditions as above. Fractions containing the product were combined and evaporated to yield a solid which was recrystallized from $CH_2Cl_2$/isopropanol to yield the desired product, m.p. 245°–250° C.

EXAMPLE 4

Preparation of
1-(1,2-dihydro-4-hydroxy-1-phenyl-2-oxo-1,8-naphthyridin-3-yl)-1-methyl-pyrrolidinium chloride 1-(1,2-dihydro-4-hydroxy-1-phenyl-2-oxo-1,8-naphthyridin-3-yl)-1-methyl-pyrrolidinium hydroxide, inner salt (0.1 g) was dissolved in 0.1 N—HCl solution (38 mL). The solution was concentrated under high vacuum to provide an oil which crystallized on the addition of isopropanol. The solid was filtered off and washed with isopropanol to yield the desired hydrochloride salt, m.p. 195° C.

EXAMPLE 5
Preparation of 1-(1,2-dihydro-4-hydroxy-1-phenyl-2-oxo-1,8-naphthyridin-3-yl)-pyrrolidinium hydroxide, inner salt A solution of 3-bromo-4-hydroxy-1-phenyl-1,8-naphthyridin-2(1H)-one (2 g) in a mixture of pyrrolidine (10 mL) and DMF (5 mL) was stirred and heated at 100° C. for 2 days. The resulting mixture was then cooled, diluted with $CH_2Cl_2$ (100 mL) and filtered. The solid was triturated with hot $CHCl_3$, filtered, and dried to yield the desired product, m.p. 282°–284° C.

EXAMPLE 6
Preparation of 1-(1,2-dihydro-4-hydroxy-1-phenyl-2-oxo-1,8-naphthyridin-3-yl)-4-hydroxy-piperidinium hydroxide, inner salt A solution of 3-bromo-4-hydroxy-1-phenyl-1,8-naphthyridin-2(1H)-one (1 g) in a mixture of 2,6-lutidine (5 mL) and 4-hydroxy-piperidine (3.12 g) was heated at 100° C. for 32 hours. The lutidine was removed by evaporation under high vacuum. The residue was dissolved in $CH_3CN(20)$: $H_2O(80)$: $CH_3CO_2H(1)$ and separated by reversed phase preparative HPLC (Whatman Magnum 40 with Partisil 40/ODS-3). The fractions containing the desired product were combined and evaporated to yield a partially crystalline material which was recrystallized from isopropanol to yield the desired product, m.p. 256°–258° C.

The following compounds were also prepared by the techniques similar to those described above:

1-(1,2-dihydro-4-hydroxy-1-phenyl-2-oxo-1,8-naphthyridin-3-yl)quinuclidinium hydroxide, inner salt, hemihydrate, m.p. >290° C.

1-methyl-1-(1,2-dihydro-4-hydroxy-1-phenyl-2-oxo-1,8-naphthyridin-3-yl)-morpholinium hydroxide, inner salt, hemihydrate, m.p. 248°–249° C.

1-(1,2-dihydro-4-hydroxy-1-phenyl-2-oxo-1,8-naphthyridin-3-yl)-piperidinium hydroxide, inner salt, hemihydrate, m.p. 261°–263° C. (decomp.).

1-(1,2-dihydro-4-hydroxy-1-phenyl-2-oxo-1,8-naphthyridin-3-yl)-2-hydroxymethyl piperidinium hydroxide, inner salt, hemihydrate, m.p. 135°–138° C.

By employing procedures similar to those described above in Examples 3, 4, 5 and 6 with simple modifications well known to one skilled in the art, the compounds 3-bromo-4-hydroxy-1-(2-pyrazinyl)-1,8-naphthyridin-2(1H)-one, 3-bromo-4-hydroxy-1-(4-pyrimidinyl)-1,8-naphthyridin-2(1H)-one, 3-bromo-1-(3-chlorophenyl)-4-hydroxy-1,8-naphthyridin-2(1H)-one, 3-bromo-4-hydroxy-1-(3-(1,2,4-triazinyl))-1,8-naphthyridin-2(1H)-one, and 3-bromo-4-hydroxy-1-(2-thienylmethyl)-1,8-naphthyridin-2(1H)-one can be converted to 1-[1,2-dihydro-4-hydroxy-2-oxo-1-(2-pyrazinyl)-1,8-naphthyridin-3-yl]-1-methyl-pyrrolidinium hydroxide, inner salt, 1-[1,2-dihydro-4-hydroxy-2-oxo-1-(4-pyrimidinyl)-1,8-naphthyridin-3-yl]-1-methylpiperidinium hydroxide, inner salt, 1-[1-(3-chlorophenyl)-1,2-dihydro-4-hydroxy-2-oxo-1,8-naphthyridin-3-yl]-1-methylpyrrolidinium hydroxide, inner salt, 1-[1,2-dihydro-4-hydroxy-2-oxo-1-(3-(1,2,4-triazinyl))-1,8-naphthyridin-3-yl]pyrrolidinium hydroxide, inner salt, and 1-(1,2-dihydro-4-hydroxy-2-oxo-1-(2-thienylmethyl)-1,8-naphthyridin-3-yl]piperidinium hydroxide, inner salt, respectively.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the structural formula I

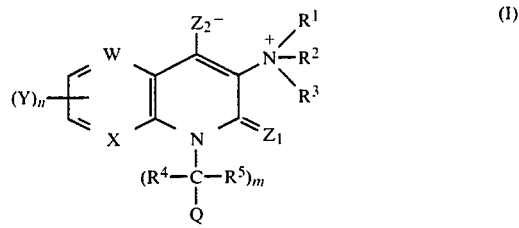

and pharmaceutically acceptable salts thereof, wherein:

X represents $-N=$ and W represents $-CH=$ or $-N=$;

$Z_1$ and $Z_2$ are the same or different and each independently represents $-O-$ or $-S-$;

$R^1$, $R^2$, $R^3$, $R^4$ and $R^5$ are the same or different and each may be independently selected from the group consisting of H, alkyl having from 1 to 12 carbon atoms, alkenyl having from 3 to 8 carbon atoms, alkynyl having from 3 to 8 carbon atoms, alkoxyalkyl having from 1 to 6 carbon atoms in the alkoxy portion and from 2 to 6 atoms in the alkyl portion thereof, hydroxyalkyl having from 2 to 8 carbon atoms, cycloalkyl having from 3 to 8 carbon atoms, acyloxyalkyl having from 1 to 6 carbon atoms in the acyloxy portion and from 2 to 8 carbon atoms in teh alkyl portion thereof, and $-R^6-CO_2R^0$ wherein $R^6$ represents an alkylene group having from 1 to 6 carbon atoms and $R^0$ represents hydrogen or an alkyl group having from 1 to 6 carbon atoms, with the provisos that the OH of the hydroxyalkyl group and the acyloxy of the acyloxyalkyl group are not joined to the same carbon atom as another heteroatom and that, when $R^1$, $R^2$ and/or $R^3$ are alkenyl or alkynyl, there is at least one carbon-carbon single bond between the nitrogen atom and the carbon-carbon double or triple bond;

in addition, one of $R^1$, $R^2$ or $R^3$ can be an aryl group which contains 6 to 15 atoms or an aromatic heterocyclic group which contains 4 to 14 carbon atoms, either of which can be substituted with one to three substituents Y as defined below;

in further addition, two of $R^1$, $R^2$ and $R^3$ can be joined together to represent an imdazolyl ring or to represent a ring which can contain from 2 to 8 carbon atoms, said ring optionally containing a —O—, —S— and/or —NR⁴— heteroatomic group (wherein R⁴ is as defined above ) and/or optionally containing a carbon-carbon double bond, and said ring optionally being substituted with one to three additional substituents $R^7$ which substituents may be the same or different and are each independently selected from OH with the proviso that OH is not on a carbon already joined to a hereto atom, —O—acyl having from 1 to 6 atoms; hydroxyalkyl having from 1 to 8 carbon atoms, alkoxyalkyl having from 1 to 6 carbon atoms in each alkyl portion thereof, alkyl having from 1 to 6 carbon atoms, alkenyl having from 3 to 8 carbon atoms, alkynyl having from 3 to 8 carbon atoms, or any two $R^7$ substituent groups may represent a hydrocarbon ring having from 4 to 8 total carbon atoms;

in still further addition, all three of $R^1$, $R^2$ and $R^3$ can be joined together to represent a polycyclic ring, which polycyclic ring can optionally be substituted by one to three substituents groups $R^7$ as defined above;

m is an integer of from 0 to 3;

n is an integer of from 0 to 2;

Q represents an aryl or an aromatic heterocyclic group which can optionally be substituted with 1 to 3 substituents Y as defined below;

each Y substituent is independently selected from the group consisting of hydroxy, alkyl having from 1 to 6 carbon atoms, halogen, $NO_2$, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, hydroxyalkyl having from 1 to 6 carbon atoms, —S-(O)$_n$—$R^8$ (wherein $R^8$ represents alkyl having from 1 to 6 carbon atoms and n is as defined above ), —SO₂NH₂, —CO—$R^9$ (wherein $R^9$ represents OH, —NH—$R^8$ or —O—$R^8$, where $R^8$ is as defined above), —O—B—COR⁹ (wherein B represents an alkylene group having from 1 to 4 carbon atoms and $R^9$ is as defined above ), —NH₂, —NHCHO, —NH—CO—$R^9$ (wherein $R^9$ is as defined above, with the proviso that it is not hydroxy), —N-H—COCF₃, —NH—SO₂R⁸ (wherein $R^8$ is as defined above ), and —NHSO₂CF₃.

2. A compound according to claim 1, wherein X is —N= and W is —CH=.

3. A compound according to claim 2, wherein at least one of $Z_1$ and $Z_2$ is O.

4. A compound according to claim 2, wherein $Z_1$ and $Z_2$ both are O.

5. A compound according to claim 3, wherein n is 0.

6. A compound according to claim 5, wherein m is 0.

7. A compound according to claim 6, wherein Q is an aryl group, which may optionally be substituted with one to three Y groups.

8. A compound according to claim 7, wherein Q is an aryl group, which may optionally be substituted with one or two Y groups.

9. A compound selected from:
1-(1,2-dihydro-4-hydroxy-1-phenyl-2-oxo-1,8-naphthyridin-3-yl)-1-methyl-pyrrolidinium hydroxide, inner salt;
1-(1,2-dihydro-4-hydroxy-1-phenyl-2-oxo-1,8-naphthyridin-3-yl)pyrrolidinium hydroxide, inner salt;
1-(1,2-dihydro-4-hydroxy-1-phenyl-2-oxo-1,8-naphthyridin-3-yl)-4-hydroxy-piperidinium hydroxide, inner salt;
1-(1,2-dihydro-4-hydroxy-1-phenyl-2-oxo-1,8-naphthridin-3-yl)quinuclidinium hydroxide, inner salt;
1-(1,2-dihydro-4-hydroxy-1-phenyl-2-oxo-1,8-naphthridin-3-yl)-1-methyl-morpholinium hydroxide, inner salt;
1-(1,2-dihydro-4-hydroxy-1-phenyl-2-oxo-1,8-naphthyridin-3-yl)piperidinium hydroxide, inner salt; or
1-(1,2-dihydro-4-hydroxy-1-phenyl-2-oxo-1,8-naphthyridin-3-yl)-2-hydroxymethyl-piperidinium hydroxide, inner salt; or a pharmaceutically acceptable salt thereof.

10. A compound having the name 1-(1,2-dihydro-4-hydroxy-1-phenyl-2-oxo-1,8-naphthyridin-3-yl)-1-methyl-pyrrolidinium hydroxide, inner salt and pharmaceutically acceptable salts thereof.

11. A compound having the same 1-(1,2-dihydro-4-hydroxy-1-phenyl-2-oxo-1,8-napthyridin-3-yl)pyrrolidinium hydoxide, inner salt or a pharmaceutically acceptable salt thereof.

* * * * *